United States Patent [19]
DeCato

[11] Patent Number: 5,869,000
[45] Date of Patent: Feb. 9, 1999

[54] PARTIAL VAPOR REMOVAL THROUGH EXHAUST PORT

[75] Inventor: Kevin Richard DeCato, Dana Point, Calif.

[73] Assignee: Johnson & Johnson Medical, Inc., New Brunswick, N.J.

[21] Appl. No.: 879,446

[22] Filed: Jun. 20, 1997

[51] Int. Cl.⁶ ............................................ A61L 9/00
[52] U.S. Cl. ................. 422/33; 422/23; 422/28; 422/292; 422/300
[58] Field of Search ................. 422/1, 21, 23, 422/28, 33, 186, 292, 294, 300, 305, 307, 906

[56] References Cited

U.S. PATENT DOCUMENTS

| | | |
|---|---|---|
| 4,169,123 | 9/1979 | Moore et al. . |
| 4,169,124 | 9/1979 | Forstrom et al. . |
| 4,643,876 | 2/1987 | Jacobs et al. . |
| 4,756,882 | 7/1988 | Jacobs et al. . |
| 4,943,414 | 7/1990 | Jacobs et al. . |
| 4,952,370 | 8/1990 | Cummings et al. . |
| 5,087,418 | 2/1992 | Jacob . |
| 5,115,166 | 5/1992 | Campbell et al. . |
| 5,492,672 | 2/1996 | Childers et al. . |
| 5,527,508 | 6/1996 | Childers et al. . |
| 5,534,221 | 7/1996 | Hillebrenner et al. . |
| 5,556,607 | 9/1996 | Childers et al. . |

FOREIGN PATENT DOCUMENTS

| | | |
|---|---|---|
| 0 302 419 A2 | 2/1989 | European Pat. Off. . |
| 0 456 135 A2 | 11/1991 | European Pat. Off. . |
| 41 02 055 A1 | 8/1991 | Germany . |

*Primary Examiner*—Krisanne Thornton
*Attorney, Agent, or Firm*—Knobbe, Martens, Olson, & Bear, LLP

[57] ABSTRACT

An apparatus and method for vapor sterilization of articles such as medical devices and instruments with lumens. The lumens are connected in a sterilization chamber to a conduit which leads to an exhaust flow restrictor, which exhausts to a vacuum pump. The exhaust flow restrictor has a bypass also which exhausts to the vacuum pump. The majority of the gas from the sterilization chamber flows through the bypass on the exhaust flow restrictor while only a portion of the gas flows through the lumen. Because most of the gas flows through the bypass rather than through the lumens, the sterilization chamber can be pumped down rapidly. The attached lumens are sterilized effectively in spite of the rapid pumpdown rate.

37 Claims, 9 Drawing Sheets

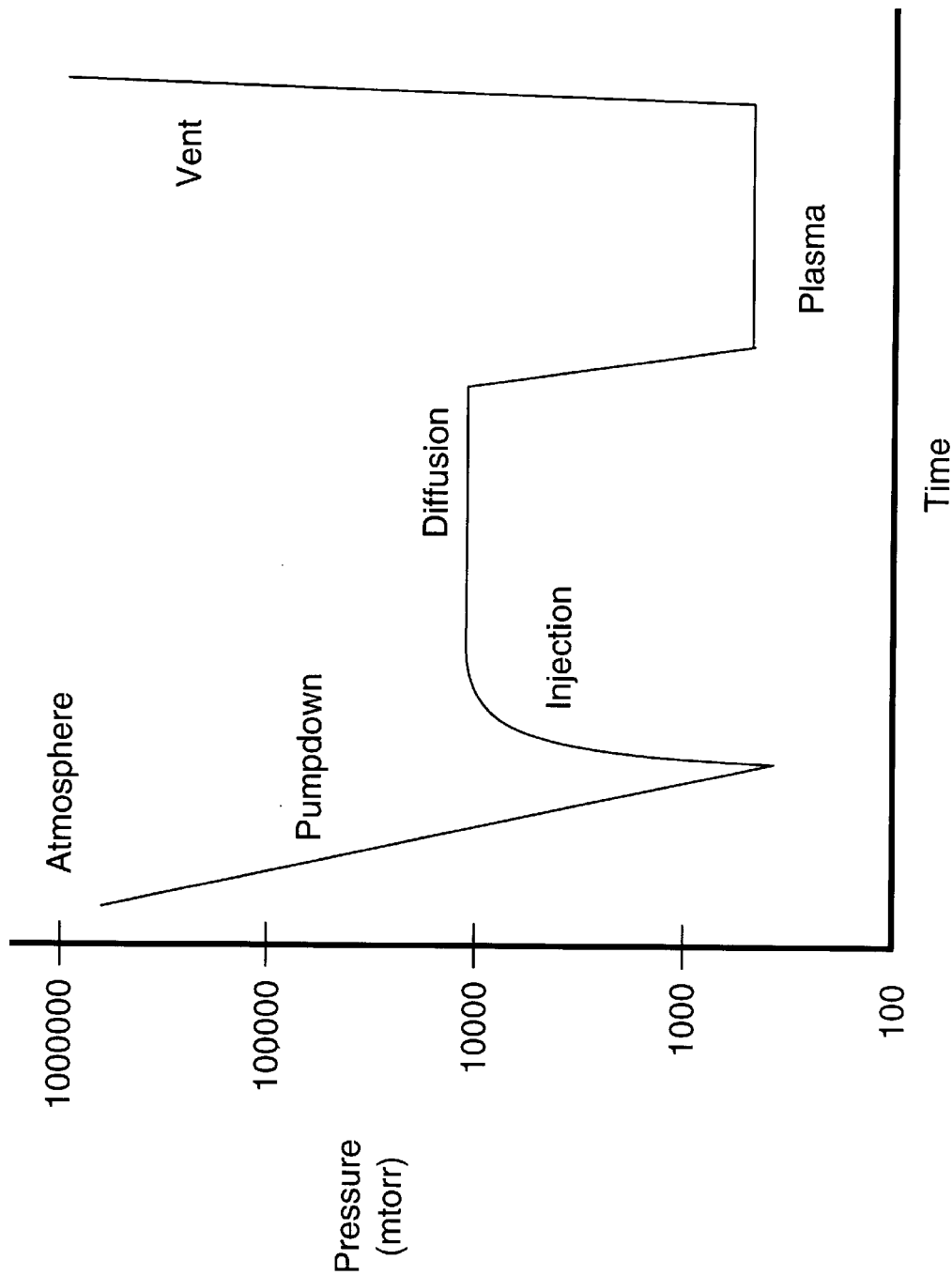
Figure 10  Example of Sterilization Cycle Process Curve

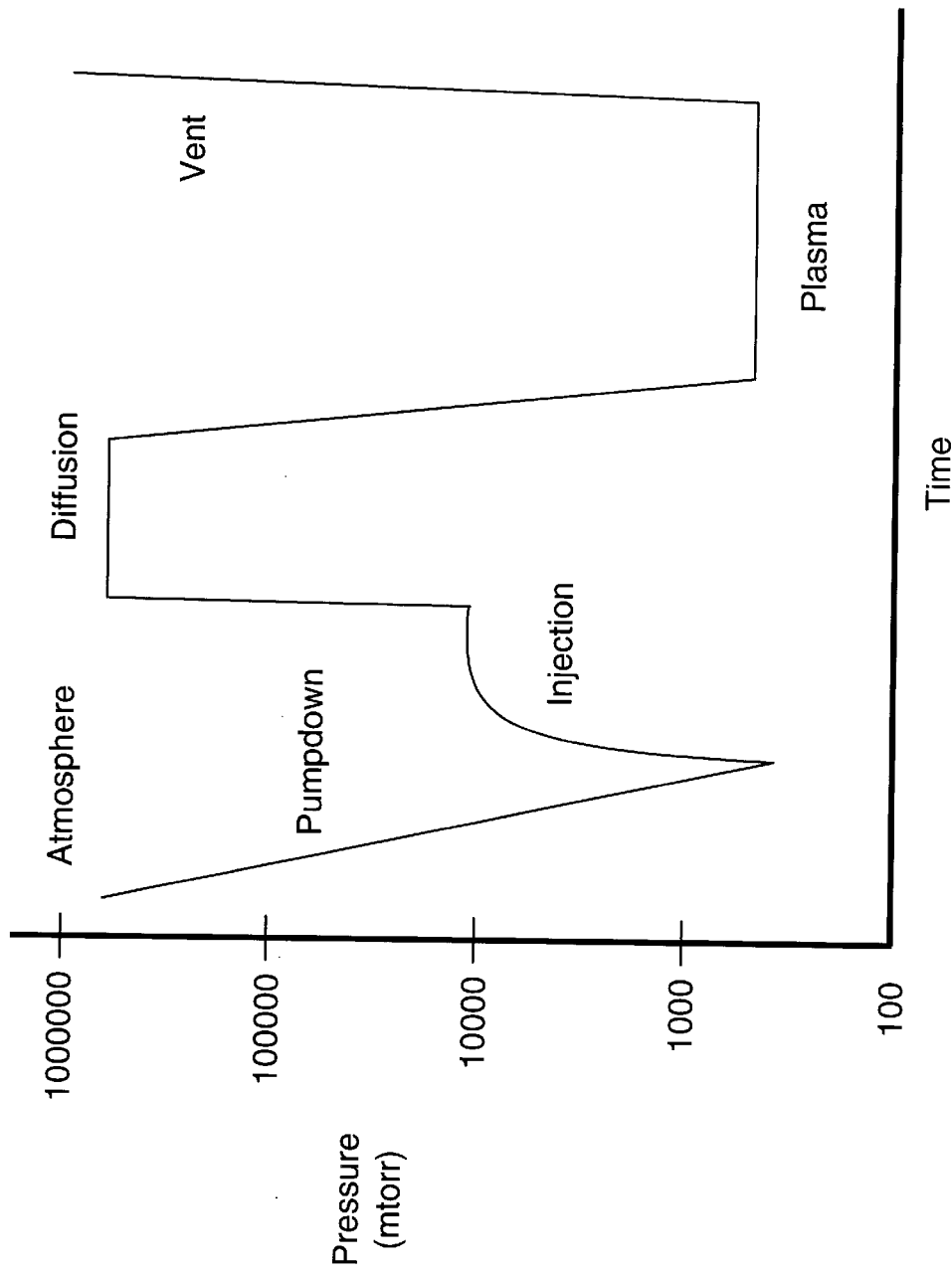
Figure 11 Example of Sterilization Cycle Process Curve

PARTIAL VAPOR REMOVAL THROUGH EXHAUST PORT

BACKGROUND OF THE INVENTION

1. Field of the Invention

The invention relates to the vapor sterilization of articles such as medical devices with at least two open ends and a flow path therebetween, and more particularly, to a device and method for delivering a high flow of vapor sterilant into and through a lumen device with at least two openings and a flow path therebetween during the sterilization process.

2. Description of the Related Art

Medical instruments have traditionally been sterilized using either heat, such as is provided by steam, or a chemical, such as formaldehyde or ethylene oxide in the gas or vapor state. Each of these methods has drawbacks. Many medical devices, such as fiberoptic devices, endoscopes, power tools, etc. are sensitive to heat, moisture, or both. Formaldehyde and ethylene oxide are both toxic gases that pose a potential hazard to healthcare workers. Problems with ethylene oxide are particularly severe, because its use requires long aeration times to remove the gas from articles that have been sterilized. This makes the sterilization cycle time undesirably long.

Sterilization using liquid hydrogen peroxide solution has been found to require high concentration of sterilant, extended exposure time and/or elevated temperatures. However, sterilization using hydrogen peroxide vapor has been shown to have some advantages over other chemical sterilization processes.

In U.S. Pat. Nos. 4,169,123 and 4,169,124 sterilization methods are disclosed using hydrogen peroxide vapor at temperatures below 80° C. Liquid hydrogen peroxide is vaporized and the hydrogen peroxide vapor is then introduced into the sterilization chamber by pressure differential.

The combination of hydrogen peroxide with a plasma provides certain additional advantages, as disclosed in U.S. Pat. No. 4,643,876, issued Feb. 17, 1987 to Jacobs et al. U.S. Pat. No. 4,756,882, issued Jul. 12, 1988 also to Jacobs et al. discloses the use of hydrogen peroxide vapor, generated from an aqueous solution of hydrogen peroxide, as a precursor of the reactive species generated by a plasma generator. The combination of hydrogen peroxide vapor diffusing into close proximity with the article to be sterilized and plasma acts to sterilize the articles, even within closed packages. Further, these methods of combining hydrogen peroxide vapor with a plasma, while useful in "open" systems, have been found to be inadequate to effect sterilization in articles having long narrow lumens, since the methods are dependent upon diffusion of the sterilant vapor into close proximity with the article before sterilization can be achieved. Thus, these methods have been found to require high concentration of sterilant, extended exposure time and/or elevated temperatures when used on long, narrow lumens. For example, lumens longer than 27 cm and/or having an internal diameter of less than 0.3 cm have been particularly difficult to sterilize.

The sterilization of articles containing long narrow lumens therefore presents a special challenge. Methods that use hydrogen peroxide vapor that has been generated from an aqueous solution of hydrogen peroxide have certain disadvantages, because:

1. Water has a higher vapor pressure than hydrogen peroxide and will vaporize faster than hydrogen peroxide from an aqueous solution.
2. Water has a lower molecular weight than hydrogen peroxide and will diffuse faster than hydrogen peroxide in the vapor state.

Because of this, when an aqueous solution of hydrogen peroxide is vaporized in the area surrounding the items to be sterilized, the water reaches the items first and in higher concentration. The water vapor therefore becomes a barrier to the penetration of hydrogen peroxide vapor into areas such as long narrow lumens. One cannot solve the problem by removing water from the aqueous solution and using more concentrated hydrogen peroxide, since, among other reasons, concentrated solutions of hydrogen peroxide greater than 65% by weight can be hazardous due to the oxidizing nature thereof.

U.S. Pat. No. 4,952,370 to Cummings et al. discloses a sterilization process wherein aqueous hydrogen peroxide vapor is first condensed on the article to be sterilized, and then a source of vacuum is applied to the sterilization chamber to evaporate the water and hydrogen peroxide from the article. This method is suitable to sterilize surfaces, however, it is ineffective at rapidly sterilizing lumened devices, since it too depends on the diffusion of the hydrogen peroxide vapor into the lumen to effect sterilization.

U.S. Pat. No. 4,943,414, entitled "Method for Vapor Sterilization of Articles Having Lumens," and issued to Jacobs et al., discloses a process in which a vessel containing a small amount of a vaporizable liquid sterilant solution is attached to a lumen, and the sterilant vaporizes and flows directly into the lumen of the article as the pressure is reduced during the sterilization cycle. This system has the advantage that the water and hydrogen peroxide vapor are pulled through the lumen by the pressure differential that exists, increasing the sterilization rate for lumens, but it has the disadvantage that the vessel needs to be attached to each lumen to be sterilized.

In U.S. Pat. Nos. 5,492,672 and 5,556,607 to Childers et al, there is disclosed a process and apparatus respectively for sterilizing narrow lumens. This process and apparatus uses a multicomponent sterilant vapor and requires successive alternating periods of flow of sterilant vapor and discontinuance of such flow. A complex apparatus is used to accomplish the method. Additionally, the process and apparatus of U.S. Pat. Nos. 5,492,672 and 5,556,607 require maintaining the pressure in the sterilization chamber at a predetermined subatmospheric pressure.

In U.S. Pat. No. 5,527,508 to Childers et al., a method of enhancing the penetration of low vapor pressure chemical vapor sterilants into the apertures and openings of complex objects is disclosed. The method repeatedly introduces air or an inert gas into the closed sterilization chamber in an amount effective to raise the pressure to a subatmospheric pressure to drive the diffused sterilant vapor further into the article to achieve sterilization. The U.S. Pat. Nos. 5,527,508, 5,492,672 and 5,556,607 inventions are similar in that all three require repeated pulsations of sterilant vapor flow and maintenance of the sterilization chamber pressure at a predetermined subatmospheric pressure.

In U.S. Pat. No. 5,534,221 to Hillebrenner et al., a device and method for sterilizing and storing an endoscope or other lumened medical device is disclosed. The device includes a sealable cassette in which the endoscope or other medical device is placed. The cassette has an input port for receiving a sterilizing agent through a connector, an output port for expelling the sterilizing agent when a vacuum is applied thereto through a connector, and check valves in the input and output ports to open the ports when the connectors are coupled to the ports and to seal the ports when the connectors are removed from the ports such that after the endoscope has been sterilized, it remains sterilized within the cassette until the cassette is opened. The method of the U.S. Pat. No. 5,534,221 invention involves placing the medical device inside the cassette and coupling the device to either the input or output port of the cassette. The cassette is then placed in an outer oven-like container or warming chamber where the temperature is properly maintained. Connections are made to open the input and output ports on the cassette such that the sterilizing agent may be introduced through a first port to bathe the outside of the medical instrument or other object, such as an endoscope while one end of the hollow object, such as the endoscope, is coupled to the output port where a vacuum is supplied external to the cassette to pull the sterilization agent into the cassette and through the interior passageways of the endoscope. When the sterilization process is completed, the warming chamber is opened and the sterilizing cassette is simply removed from the chamber with the input and output ports being uncoupled from their respective sources. A tight seal is maintained and the object remains in the sterilized interior of the cassette until the cassette is opened or the device is to be used. The inlet and outlet ports also provide a means to supply and remove air and/or other fluids to and from the cassette during other non-sterilization phases of the process, such as warm-up and aeration. Plasma treatment steps are not included in U.S. Pat. Nos. 5,534,221 methods. Thus, the U.S. Pat. No. 5,534,221 invention is concerned with providing a means whereby a sterilized medical device can be retained within a cassette in which it was sterilized until ready for use, thus avoiding any contamination by exposure to the atmosphere or handling before use. Additionally, in some cases of the U.S. Pat. No. 5,534,221 invention, wherein the lumen of the device to be sterilized is connected to the output port, particularly wherein the devices have long, narrow lumens, the time to expel the sterilizing agent through the lumen and out of the cassette may be undesireably long. Also, in cases wherein the lumen device is very flexible, lumen collapse may occur, either slowing or preventing vapor exit or causing lumen damage.

Thus, no simple, safe, effective method of sterilizing smaller lumens exists in the prior art. In consideration of the foregoing, there remains a need for a simple and effective method of vapor sterilization of articles with both long, narrow lumens as well as shorter, wider lumens.

SUMMARY OF THE INVENTION

One aspect of the present invention is an apparatus for sterilizing the interior and exterior of a device with at least two open ends and a flow path therebetween, comprising:
  a sterilization chamber having an exhaust port;
  a source of liquid or vapor sterilant adapted to provide the sterilant in the sterilization chamber;
  a vacuum source with a vacuum valve to create a sterilization vapor from the sterilant, a negative pressure differential at the exhaust port of the sterilization chamber and an exhaust flow path out of the chamber;
  a gas and vapor flow conduit connecting one of the open ends of the device to a flow path of a vapor exhaust flow restrictor, such flow path allowing exhaust flow out of the sterilization chamber through the vacuum valve and vacuum source; and
  a vapor exhaust flow restrictor which allows part of the sterilization vapor to flow through the flow path of the device and thereafter out of the sterilization chamber through the vacuum valve and vacuum source and the remainder of the sterilization vapor to flow directly out of the sterilization chamber through the vacuum valve and vacuum source without passing through the flow path of the device.

In one embodiment of the apparatus, the device is a lumen. In another embodiment of the apparatus, the sterilant is from the group consisting of hydrogen peroxide and peracetic acid. In another embodiment of the apparatus, the source of sterilant is selected from the group consisting of an injector, a liquid flow-through device, a liquid reservoir or aerosol spray device. In another embodiment of the apparatus, the source of sterilant is placed inside the chamber. Preferably, the source of sterilant placed inside the chamber is a liquid reservoir placed inside the chamber. In another embodiment of the apparatus of the invention, the gas and vapor flow conduit is constructed for releasable connection. In a preferred embodiment, the gas and vapor flow conduit constructed for releasable connection connects one of two open ends of multiple devices simultaneously to a flow path of the vapor exhaust flow restrictor, the flow path allowing exhaust flow out of the sterilization chamber through the vacuum valve and vacuum source. In another embodiment of the apparatus of the invention, the vapor exhaust flow restrictor contains first and second flow paths, wherein the first and second flow paths each have an opening with an opening area, and wherein the first flow path is a continuously open flow path opened to flow in both directions and which allows exhaust flow out of the sterilization chamber through the vacuum valve and vacuum source. In a preferred embodiment of the aforementioned apparatus of the invention, the first flow path is constructed with multiple conduits connected to the sterilization chamber side of the flow path, wherein the conduits allow air venting and exhaust flow into and out of said chamber respectively, from more than one location inside the chamber. In a preferred embodiment of the aforementioned apparatus of the invention, the first flow path further comprises a valve, the valve being capable of opening or closing the first flow path. In a preferred embodiment of the aforementioned apparatus of the invention, the second flow path allows flow only in the direction of the sterilization chamber exhaust port, allowing exhaust flow out of the sterilization chamber through the vacuum valve and vacuum source and which does not allow the influx of air from outside the sterilization chamber and wherein the second flow path is connected to the gas and vapor flow conduit and through the conduit to one of the two open ends of the device to be sterilized. In a preferred embodiment, the ratio of the flow of the first flow path to the flow of the second flow path is such that the sterilization vapor exhaust flow through the first and second flow paths results in maximum efficiency of sterilization of the device to be sterilized. In another preferred embodiment of the aforementioned apparatus, the ratio of the opening area of the first flow path to the opening area of the second flow path is between 1.0 and 2.0. In another preferred embodiment of the aforementioned apparatus, the ratio of the opening area of the first flow path to the opening area of the second flow path is 1.65. In another preferred embodiment of the aforementioned apparatus, the vapor exhaust flow restrictor has more than one opening for each flow path. In another embodiment of the apparatus of the invention, the vacuum source is a vacuum pump. In another embodiment of the apparatus of the invention, the sterility of the device is maintained following sterilization with an enclosure, wherein the enclosure completely encloses the device. Preferably, the enclosure comprises a flexible material. Preferably, the flexible material is comprised of non-woven polypropylene.

In another aspect of the invention, a method is provided for sterilizing the interior and exterior of a device with at least two open ends and a flow path therebetween, comprising the steps of:

placing the device into a sterilization chamber having an exhaust port;

connecting one of the open ends of the device to a first end of a gas and vapor flow conduit having a first and second end, the second end of which is connected to a flow path of a vapor exhaust flow restrictor, the flow path of the vapor exhaust flow restrictor allowing exhaust flow out of the sterilization chamber through a vacuum valve and vacuum source;

introducing a liquid or vapor sterilant into the sterilization chamber;

exposing the device to negative pressure with the use of the vacuum source for a time sufficient to provide sterilization vapor directly to the interior and exterior of the device, wherein the exposing can be before or after the introducing step; and exposing the device to negative pressure with the use of the vacuum source to create a negative pressure differential at the exhaust port of the sterilization chamber and the use of the vapor exhaust flow restrictor for a time sufficient so that part of the sterilization vapor flows through the flow path of the device and out of the sterilization chamber and the remainder of the sterilization vapor flows directly out of the sterilization chamber without passing through the flow path of the device whereby the device is sterilized.

In one embodiment of the method, the device is a lumen. In yet another embodiment of the method, the sterilant is from the group consisting of hydrogen peroxide and peracetic acid. In yet another embodiment of the method, the introducing of the sterilant comprises delivery via one or more methods selected from the group consisting of injection, liquid flow-through, a liquid reservoir and aerosol spray. Yet another embodiment of the method further comprises the step of exposing the device to a plasma after the first exposing step or prior to or after the second exposing step. Preferably, the plasma is generated in a second, separate chamber and the method further comprises the step of flowing the plasma into the sterilization chamber. Another embodiment of the method of the invention further comprises warming the device to be sterilized in the sterilization chamber prior to the introducing step. Preferably, the device to be warmed is warmed with an applied electric field at low pressure. Preferably, the device is exposed to a plasma following the step of exposing the device to negative pressure with the use of the vacuum source. In a preferred embodiment of the aforementioned method further comprising the step of exposing the device to a plasma following the negative pressure exposing step, the plasma is generated in a second separate chamber and the method further comprises the step of flowing the plasma into the sterilization chamber. Another embodiment of the method of the invention further comprises the step of enclosing the device completely in an enclosure prior to placing the device into a sterilization chamber to maintain the sterility of the device following sterilization. Preferably, the enclosure is comprised of nonwoven polypropylene. In another embodiment of the basic method of the invention, all of the steps of the method of the invention following the connecting step are repeated one or more times. Another embodiment of the basic method of the invention further comprises the step between the negative pressure exposing steps of venting air directly into the sterilization chamber or alternatively through a flow path in the vapor exhaust flow restrictor, wherein the flow path is continuously open to the sterilization chamber, for a time sufficient for the air and sterilization vapor mixture to come in close contact with the device to be sterilized. In another embodiment of the method of the invention comprising an air venting step, all of the steps of the method of the invention following the connection step are repeated one or more times.

BRIEF DESCRIPTION OF THE DRAWINGS

FIG. 10 is a graph of one embodiment of the sterilization cycle of the present invention; and FIG. 11 is a graph of a second embodiment of the sterilization cycle of the present invention.

DETAILED DESCRIPTION OF THE PREFERRED EMBODIMENT

Figure 1:
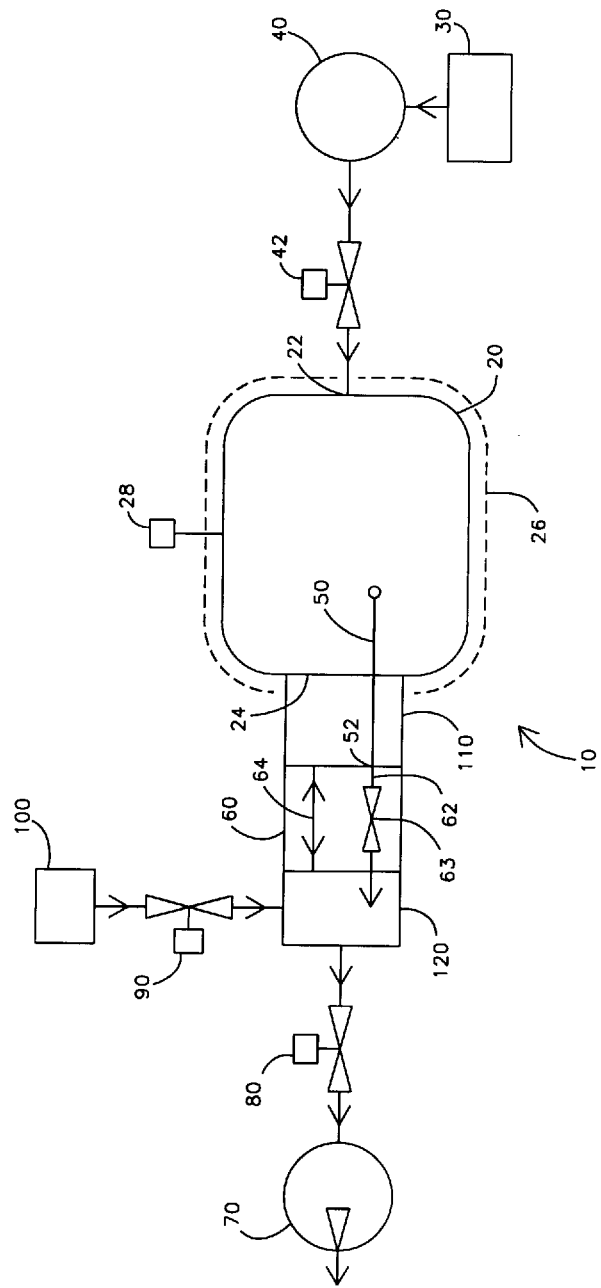
FIG. 1 is a schematic diagram of one embodiment of a sterilizer in which the method of the present invention can be practiced.

The present invention comprises an apparatus and method for sterilizing the interior and exterior of a device, such as a medical device with a lumen having at least two open ends and a flow path therebetween. The apparatus and method are intended for use with vapor sterilization procedures. In the procedures of the present invention, the device to be sterilized is placed within a sterilization chamber having an exhaust port and one open end of the device is connected via a conduit to one flow path of a vapor exhaust flow restrictor, such flow path allowing exhaust flow out of the sterilization chamber through a vacuum valve and vacuum source. The pressure in the chamber is reduced, and a liquid sterilant is introduced into the chamber where it vaporizes. Alternatively, the liquid sterilant may be introduced into the sterilization chamber prior to reducing the pressure in the chamber. Alternatively, a sterilant vapor may be introduced directly into the chamber before or after the pressure therein has been reduced. In all cases, the instrument is sterilized by exposure to the vapor or active species generated from it. The sterilant vapor is allowed to contact the article for a period of time. An optional step at this time is the venting of air into the chamber through a second flow path in the vapor exhaust flow restrictor for a time sufficient for the air and sterilant vapor mixture to contact the article. Alternatively, the air may be vented directly into the sterilization chamber without going through a second flow path in the vapor exhaust flow restrictor. The volume of the air and sterilant vapor mixture at this stage is equal to the volume of the sterilization chamber. A final non-optional step involves exposing the device to negative pressure with the use of a vacuum source by drawing a vacuum through all flow paths of the vapor exhaust flow restrictor for a time sufficient so that part of the air and sterilant vapor mixture flows through the lumen of the article and out of the sterilization chamber and the remainder of the air and sterilization vapor mixture flows directly out of the sterilization chamber without passing through the lumen of the article and the article is sterilized. The procedure may further involve at any step the use of heat or, e.g., low pressure gas plasma to enhance the sterilant activity, reduce sterilization times, and/or remove any residual sterilant from the instrument. The apparatus and method of the present invention can also be utilized along with means for maintaining the sterility of devices once they have been sterilized according to the invention.

Sterilizing the inside of lumened devices has always posed a challenge to sterilization systems. Achieving rapid sterilization of lumened devices or other diffusion restricted articles at low temperatures and low concentrations of sterilant represents an even greater challenge. In the present invention, the shortcomings of the prior art sterilization systems are overcome by employing a simple apparatus and method for creating a large volume sterilization vapor flow through the sterilization chamber and the lumen. The method of the present invention does not depend upon the diffusion of sterilant vapor into the article being sterilized. Rather, the sterilant vapor is created by the vacuum and is drawn into the interior of the device to be sterilized by the apparatus and method of the invention. In addition, the apparatus and method of the invention increase the contact between the sterilant vapor and the interior of the device to be sterilized, thus serving to increase the effectiveness of sterilization. The apparatus and method of the present invention allow sterilization to be achieved in a single cycle or sterilant vapor pass without requiring multiple pulses of sterilant vapor to be pulsed through the lumen with the use of a complex apparatus, nor venting the sterilizer following the injection or vaporization of the sterilant, nor employing a special vessel to deliver sterilant vapors into the lumen. The apparatus and method of the present invention employing two exhaust flow paths also allows for rapid sterilant vapor exhaust without risking lumen damage. The apparatus and method of the present invention thus provide for the rapid sterilization of lumened articles under conditions that will not damage the articles nor leave toxic residues on the sterile articles.

FIG. 1 illustrates one embodiment of a sterilizer apparatus 10 in which the method of the present invention can be practiced. Sterilizer apparatus 10 comprises: a sterilization chamber 20, a source of liquid or vapor sterilant 30, a component 40 to introduce a liquid or vapor sterilant into the sterilization chamber 20 to provide a source of sterilant vapor to the lumen during the vapor sterilization process, a gas and vapor flow conduit 50 connecting one open end of an article to be sterilized which has at least two open ends and a flow path therebetween to one flow path of a vapor flow restrictor 60, a vacuum source 70 and three valves 42, 80 and 90. In this embodiment, the vapor exhaust flow restrictor 60 is placed between two conduits 110 and 120 connecting the exhaust port 24 of the sterilization chamber 20 with a vacuum source 70. The vapor exhaust flow restrictor 60 has a first and second flow path. The first flow path is a continuously open flow path 64 which connects the exhaust port 24 of the sterilization chamber 20 directly with the vacuum source valve 80 and the air inlet valve 90. The second flow path 62 contains a one-way valve 63 open only to flow in the direction of the vacuum source valve 80 and connects the vacuum source valve 80 and the air inlet valve 90 to the vapor exhaust flow restrictor end 52 of the gas and vapor flow conduit 50. The purpose of valve 63 is to prevent the influx of air from the vapor exhaust flow restrictor 60 direction into the lumen of an article to be sterilized. In this way, sterilant vapor already inside the lumen will not be flushed out by pure air. Rather, the air mixes with sterilant vapor already inside the chamber and the mixture is allowed to flow into the flow path or lumen of the article via the incoming air combined with vapor diffusion and thus fully contact the article to be sterilized, following which the mixture of air and sterilant vapor is allowed to flow out of the flow path or lumen of the article in the allowed direction through valve 63 and to exit the chamber.

The sterilization chamber 20 includes a liquid or vapor sterilant inlet port 22, an exhaust port 24, a heater 26 and any suitable known temperature, pressure and humidity sensors, designated collectively herein as 28. A valve 42 is positioned in the sterilant inlet line between the sterilant delivery component 40 and the sterilization chamber inlet port 22. In other embodiments, the valve 42 is positioned between the source of sterilant 30 and the sterilant delivery component 40. Suitable sterilant delivery components include an injector, a liquid flow-through device, a liquid reservoir or aerosol spray device. Valve 80 is positioned in the exhaust line between the vapor exhaust flow restrictor 60 and vacuum source 70. Vacuum source 70 is preferably a two stage vacuum pump. A valve 90 is connected to the exhaust line 120 between a HEPA filter 100 and the air inlet and vapor exhaust flow restrictor 60. The HEPA filter is used to pass only sterile air. Valve 90 can be an air break solenoid valve or an air injector valve to more carefully control the influx of air.

Figure 2:
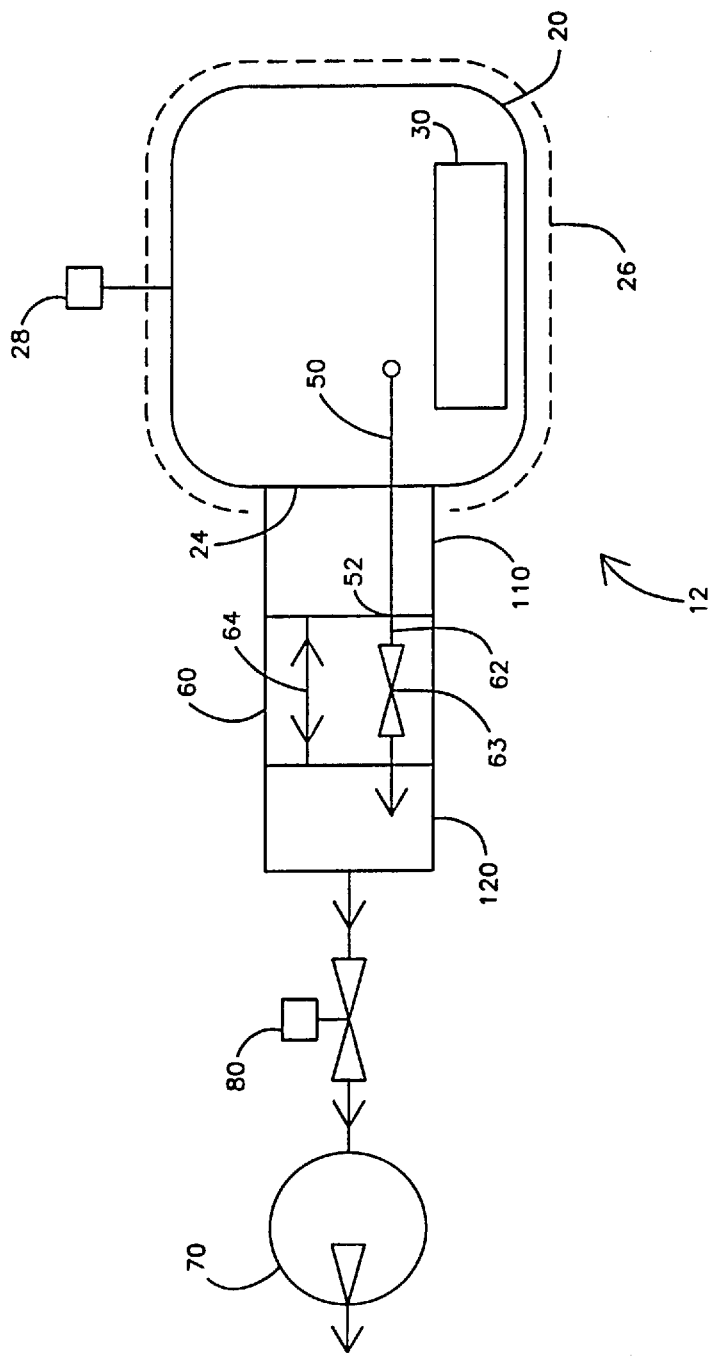
FIG. 2 is a schematic diagram of a second embodiment of a sterilizer in which the method of the present invention can be practiced.

FIG. 2 illustrates a second embodiment of a sterilizer apparatus 12 in which the method of the present invention can be practiced. A source of liquid sterilant 30 is placed directly inside sterilization chamber 20 in this embodiment. Component 40, valve 42 and inlet port 22 illustrated in FIG. 1 are therefore not necessary in this embodiment. The particular placement of air inlet valve 90 and HEPA filter 100 from FIG. 1 are not shown in this embodiment of the invention. Air inlet valve 90 can lead directly into conduit 120 as in FIG. 1 or alternatively, can lead directly into sterilization chamber 20. All other sterilizer apparatus parts shown in FIG. 2 are the same and perform the same as in FIG. 1.

The general operation of one embodiment of the method of the present invention which corresponds to the above embodiments of the apparatus of the invention illustrated in FIGS. 1 and 2 is as follows: The article to be sterilized, such as a medical device with a long narrow lumen with at least two open ends and a flow path therebetween, is placed within a sterilization chamber 20. One open end of the lumen is connected via a gas and vapor flow conduit 50 to flow path 62 of a vapor exhaust flow restrictor 60, such flow path only allowing exhaust flow out of the sterilization chamber. The vapor exhaust flow restrictor 60 is fixed in place between the exhaust port 24 of the sterilization chamber 20 and the vacuum pump valve 80. The pressure in the chamber 20 is reduced and a vapor or liquid sterilant such as aqueous hydrogen peroxide, peracetic acid or other peroxide compound at a concentration of for example 70 w/v % or lower is introduced into the chamber 20 via one or more methods selected from the group consisting of injection, liquid flow-through, a liquid reservoir and aerosol spray. No upper limit is placed on the concentration of the peroxide compound. However, a preferred concentration is less than 70% w/v. An even more preferred concentration is less than 60% w/v. The liquid sterilant delivery component may be external to the sterilization chamber or inside the chamber. An example of a liquid sterilant delivery component inside the sterilization chamber is a liquid reservoir placed inside the chamber which is open to the chamber. The liquid sterilant vaporizes and the sterilant vapor is allowed to contact the interior and exterior of the article to be sterilized for a period of time. This period of time can range from 1 to 60 minutes for a time sufficient to provide a source of sterilization vapor from a liquid sterilant and to provide sterilization vapor directly to the interior and exterior of a device such as a device with a lumen. This time is readily determined with conventional testing techniques for evaluating sterilant vapor production, diffusion and contact and overall sterilization cycle performance. An optional step at this point is the venting of air into the chamber 20 through optional valve 90 into conduit 120 leading to the vacuum pump valve 80 from the vapor exhaust flow restrictor 60 and then through a continuously open flow path 64 in the vapor exhaust flow restrictor 60. Air is vented into the chamber 20 until the pressure in the chamber 20 is about atmospheric pressure. The air and sterilant vapor mixture is allowed to fully diffuse through the lumen for an additional contact time. This period of time can range from 1 to 30 minutes for a time sufficient for the air and sterilization vapor mixture to come in close contact with said device to be sterilized. This time is again determined readily with conventional sterility testing techniques for evaluating sterilant vapor diffusion and contact and overall sterilization cycle performance. The vacuum pump 70 is turned on once again to produce a pressure between 0.1 and 1.0 Torr in chamber 20 and a sterilization vapor exhaust flow out of the sterilization chamber is created through the lumen as well as the sterilization chamber exhaust port 24 by the vapor exhaust flow restrictor 60 flow paths 62 and 64. The sterilization chamber 20 is held at this pressure for between 1 and 20 minutes for a time sufficient so that part of the sterilization vapor flows through the lumen of said device and out of the sterilization chamber and the remainder of the sterilization vapor flows directly out of the sterilization chamber without passing through the lumen of said device and said device is sterilized. The invention thus produces partial vapor removal through the lumen, insuring full contact between the sterilization vapor and the surface of the lumen and creates a large volume sterilization vapor flow through the sterilization chamber 20, sterilization chamber exhaust port 24 and the lumen, allowing sterilization to be achieved in a single cycle or sterilant vapor pass without requiring multiple pulses of sterilant vapor to be pulsed through the lumen.

An additional step or steps at any stage of the sterilization cycle may involve the generation of a low pressure gas plasma to enhance the sterilant activity, reduce sterilization times, and/or remove any residual sterilant from the instrument. When used in the present specification and claims, the term "plasma" is intended to include any portion of the gas or vapor that contains electrons, ions, free radicals, dissociated and/or excited atoms or molecules produced as a result of an applied electric field, including any accompanying radiation that might be produced. The applied field may cover a broad frequency range; however, a radio frequency or microwaves are commonly used.

The sterilization method of the present invention can also be used with plasmas generated by the method disclosed in the previously mentioned U.S. Pat. No. 4,643,876. Alternatively, it may be used with plasmas described in U.S. Pat. No. 5,115,166 or 5,087,418, in which the article to be sterilized is located in a chamber that is separated from the plasma source. An additional step of aerating the sterilization chamber following any plasma exposure step can also be used with the present invention.

The apparatus and method of the present invention can also be utilized along with means for maintaining the sterility of devices once they have been sterilized according to the invention. For example, the entire device can be wrapped or enclosed in what is known in the art as CSR wrap, which is a non-woven polypropylene material which is permeable to sterilant vapor but impermeable to microorganisms. Conventional materials known in the art other than CSR wrap can also be employed to maintain the sterility of devices once they have been sterilized. The device is completely wrapped or enclosed, including the lumen end which is connected to the gas and vapor flow conduit 50 and through that conduit to flow path 62 of a vapor exhaust flow restrictor 60. Conduit 50 can be connected to the lumen with the wrap in place. This would otherwise be akin to placing an impermeable barrier inside a conduit if the wrap were not vapor permeable.

Additionally, the device to be sterilized can first be connected to a conduit with a larger opening on one end, wherein one of the open ends of the device is connected to the smaller of the openings on the conduit, and then this entire assembly can be wrapped in CSR wrap. The end of the conduit with the larger opening, which is now covered by CSR wrap can then be inserted into a similarly sized large open end of another conduit which is connected to the gas and vapor flow conduit 50 and through conduit 50 to flow path 62 of a vapor exhaust flow resistor 60. The utility of this embodiment of maintaining the sterility of a device once it has been sterilized is that a much larger area of CSR wrap is placed in the sterilant vapor exhaust flow path and, thus, a higher and faster sterilant vapor exhaust flow can be achieved.

Yet another embodiment of maintaining the sterility of a device once it has been sterilized is the further inclusion of a spring ball valve in either the small end of the conduit connected to the gas and vapor flow conduit 50 or the end of the conduit 50 itself. In this embodiment, the corresponding conduit end which is designated to fit into the spring ball valve is appropriately sized to do so.

Yet another embodiment of maintaining the sterility of a device once it has been sterilized is the further inclusion of an O-ring in one of the above larger open ends of a conduit and a corresponding O-ring groove in the other large open end of the second conduit, wherein the O-ring and O-ring groove are designed to form a vapor and microorganism impermeable seal when the two conduits are joined together and wherein the O-ring seal system does not interfere with the flow of vapor sterilant. Alternatively, instead of an O-ring and groove system for maintaining the sterility of a device once it has been sterilized, two ring-shaped magnets can be employed, one on each of the conduit ends to be joined. Other appropriate shapes other than ring shapes can also be employed. Thus, the system can be closed or opened quickly. In lieu of two magnets, one magnet and one metal part can be utilized, as long as a vapor and microorganism impermeable seal can be formed when the two conduits are joined together and wherein the closure system does not interfere with the flow of vapor sterilant.

Figure 8A:
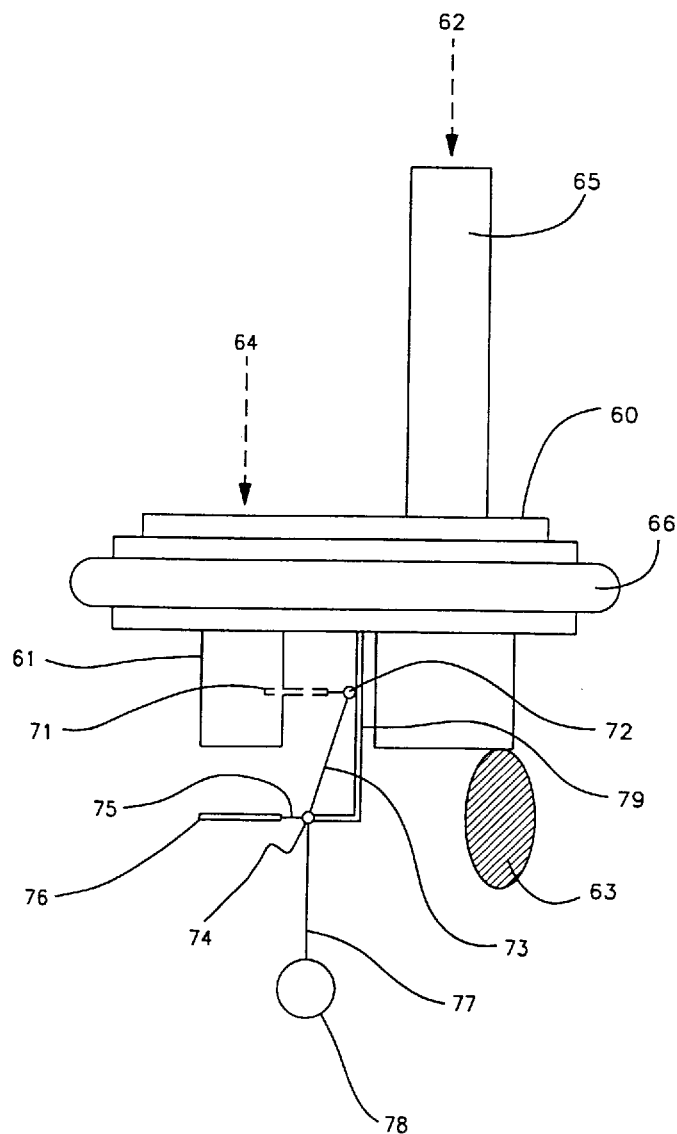
FIGS. 8A and 8B are side views of another preferred embodiment of the vapor exhaust flow restrictor of FIG. 3.
Figure 8B:
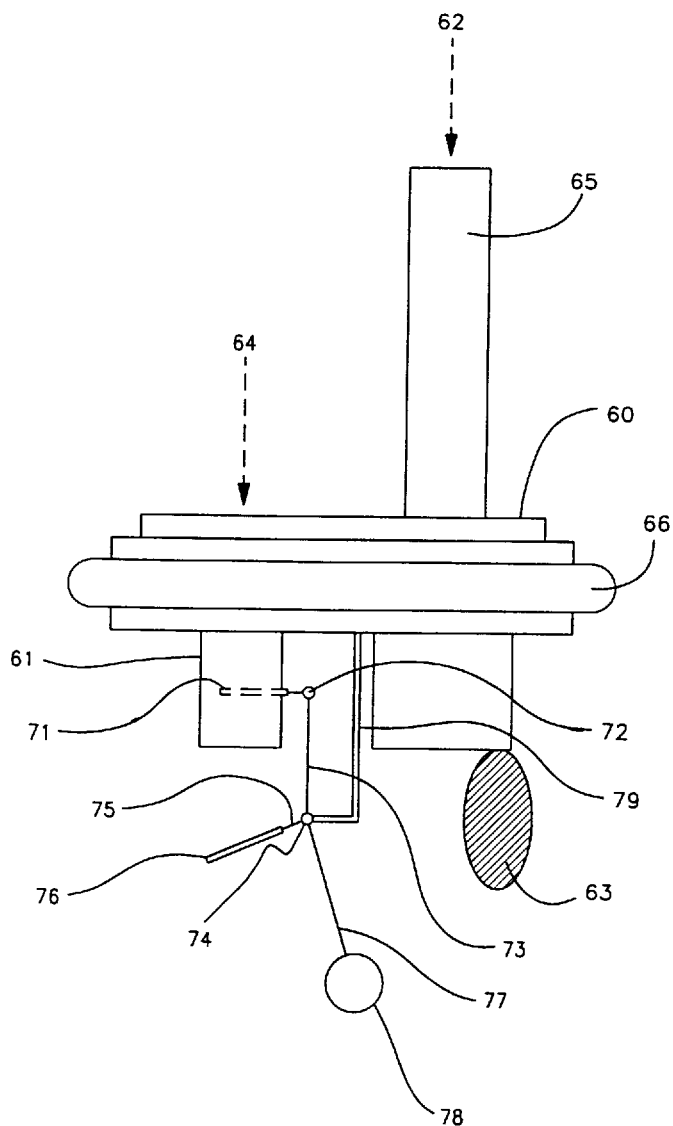
Figure 9:
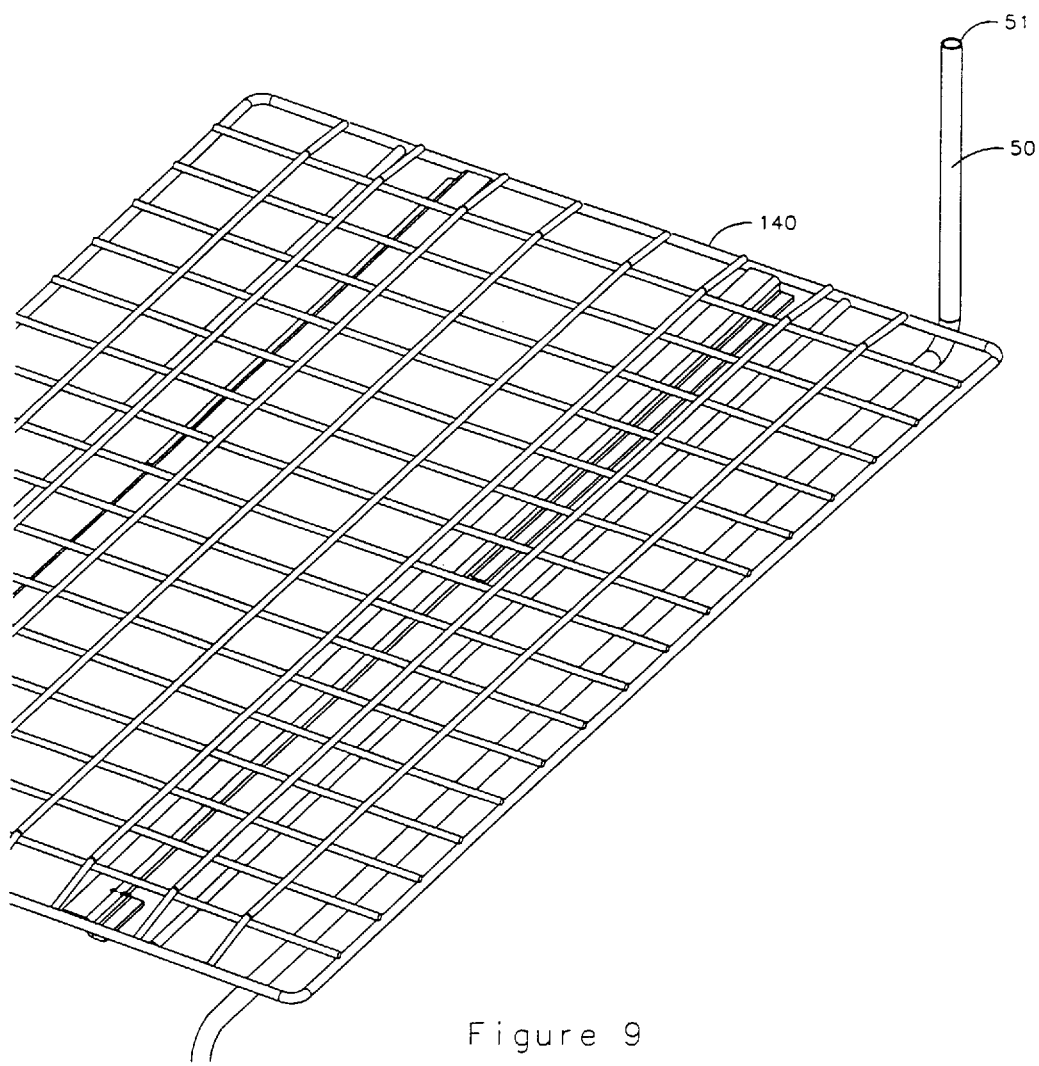
FIG. 9 is a perspective view of a preferred embodiment of the gas and vapor flow conduit of the sterilization apparatus of the invention.

Particularly preferred embodiments of the apparatus of the invention are illustrated in FIGS. 1–9. FIG. 1 is a schematic diagram of one embodiment of a sterilizer apparatus 10 in which the particularly preferred embodiments of the apparatus of the invention illustrated in FIGS. 3–9 can be utilized. FIGS. 3–8 illustrate particularly preferred embodiments of the vapor exhaust flow restrictor 60 of the sterilization apparatus 10 of the invention, showing the preferred design and placement between conduits 110 and 120 between the exhaust port 24 of the sterilization chamber 20 and the vacuum pump valve 80. FIG. 9 illustrates a preferred embodiment of the gas and vapor flow conduit 50 of the sterilization apparatus 10 of the invention.

Figure 3:
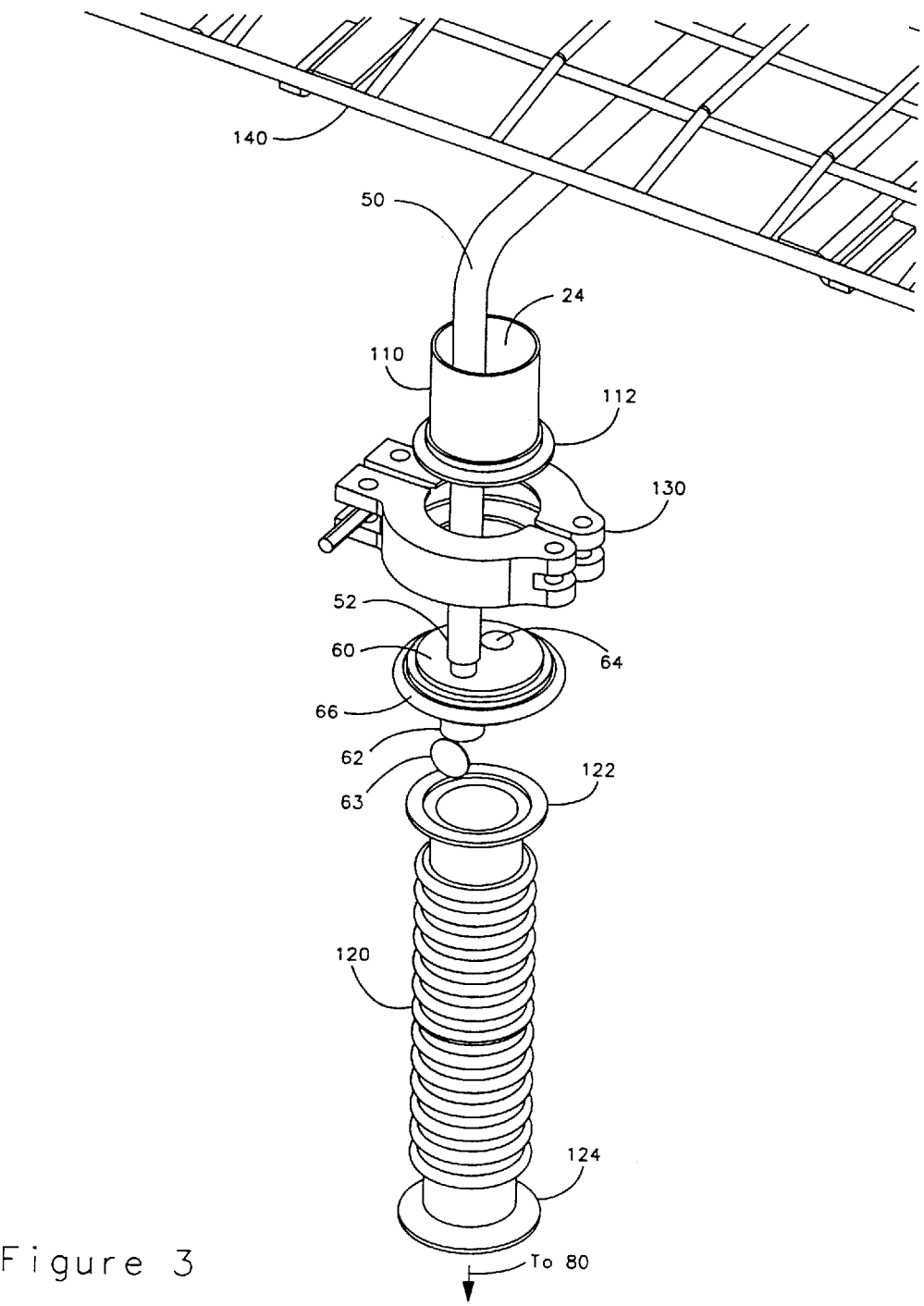
FIG. 3 is a perspective assembly view of a preferred embodiment of the vapor exhaust flow restrictor of the sterilization apparatus of the invention, showing its preferred design and placement in a conduit between the exhaust port of the sterilization chamber and the vacuum pump valve.

FIG. 3 shows the vapor exhaust flow restrictor 60, its direct connection to the vapor exhaust flow restrictor end 52 of the gas and vapor flow conduit 50, and how the flow restrictor 60 would be connected with a clamp 130 to end 112 of conduit part 110 and end 122 of conduit part 120. Here O-ring 66 on the flow restrictor 60 is pressure sealed between conduit parts 112 and 122 with clamp 130. Conduit part 110 ends in exhaust port 24 of sterilization chamber 20. Conduit part 120 leads to vacuum pump valve 80 via end 124. A rack 140 is placed inside sterilization chamber 20 and is used for holding lumen devices and other articles to be sterilized. Gas and vapor flow conduit 50 is shown running below rack 140. Sterilization chamber 20 is not shown in FIG. 3. The vapor exhaust flow restrictor 60 also includes flow path 62 with one-way valve 63 (the inside diameter of flow path 62 is not shown in FIG. 3) open to flow in the direction of the vacuum pump valve 80 only. Flow restrictor 60 also includes a continuously open flow path 64 between exhaust port 24 of sterilization chamber 20 and vacuum pump valve 80.

Figure 4:
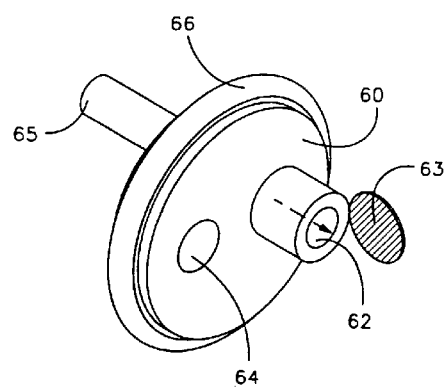
FIG. 4 is a perspective view from the vacuum source side of the preferred embodiment of the vapor exhaust flow restrictor of FIG. 3.

FIG. 4 is a perspective view from the vacuum pump valve 80 side of the preferred embodiment of the vapor exhaust flow restrictor 60 of FIG. 3. Flow path 62 with one-way valve 63 open to flow in the direction of the arrow is shown. One-way valve 63 in this embodiment is a rubber flap valve. FIG. 4 illustrates this valve in the open position. In other embodiments, other conventional valves may be employed for valve 63. Continuously open flow path 64 is shown. End 65 of a conduit leading to flow path 62 is designed with the appropriate outside diameter to fit tightly inside the vapor exhaust flow restrictor end 52 of the gas and vapor flow conduit 50 without pressure loss. The connection between ends 65 and 52 is preferably designed for releasible connection via well known designs. O-ring 66 is also shown. This is constructed of rubber materials or materials with the elastic properties of rubber known to those of ordinary skill in the art. These rubber materials need to be compatible with low pressure systems and typically do not include rubber materials of high gas permeability such as silicone rubber.

Figure 5:
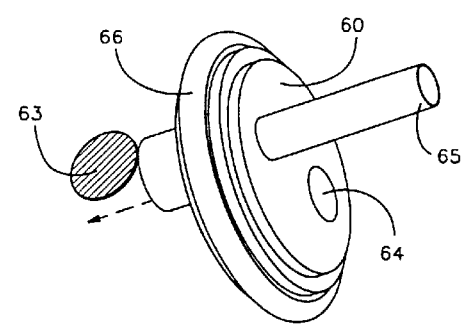
FIG. 5 is a perspective view from the sterilization chamber exhaust port side of the preferred embodiment of the vapor exhaust flow restrictor of FIG. 3.

FIG. 5 is a perspective view from the sterilization chamber exhaust port 24 side of the preferred embodiment of the vapor exhaust flow restrictor 60 of FIG. 3. The same parts with the exception of flow path 62 illustrated in FIG. 4 are shown once again in FIG. 5.

Figure 6:
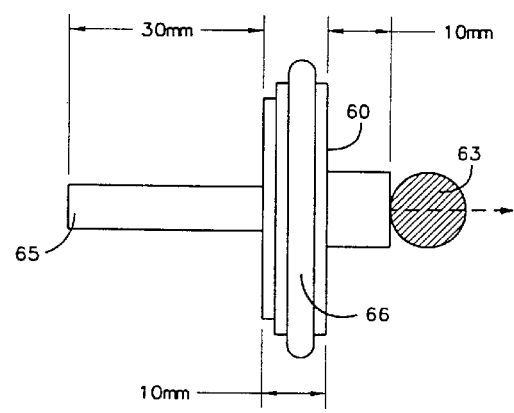
FIG. 6 is a side view of the preferred embodiment of the vapor exhaust flow restrictor of FIG. 3.

FIG. 6 is a side view of the preferred embodiment of the vapor exhaust flow restrictor 60 of FIG. 3. The same parts illustrated in FIG. 4 are shown once again in FIG. 6 with the exception of parts 62 and 64. FIG. 6 shows the dimensions in millimeters(mm) of particular aspects of the flow restrictor 60. The overall dimensions and shape are not critical and can vary for other embodiments according to the particular connection needs, e.g. conduit connection needs of conduit ends 112,122 and 52 and the particular needs of clamp 130, all of which are illustrated in FIG. 3. Note that in some embodiments, multiple conduits and a clamp may not be needed. The basic connection requirements are that the vapor exhaust flow restrictor 60 flow paths 62 and 64 be connected to the device lumen via conduit 50 and connected to the sterilization chamber exhaust port 24, the vacuum valve 80, vacuum source 70 and an optional air inlet valve 90 according to the flow path connections schematically illustrated in FIGS. 1 and 2.

Figure 7:
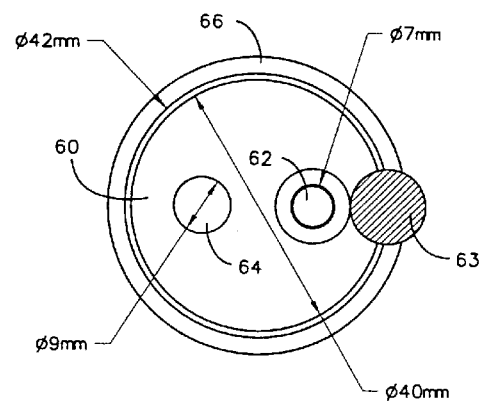
FIG. 7 is a face view from the vacuum source side of the preferred embodiment of the vapor exhaust flow restrictor of FIG. 3.

FIG. 7 is a face view from the vacuum pump 70 side of the preferred embodiment of the vapor exhaust flow restrictor 60 of FIG. 3. The same parts illustrated in FIG. 4 are shown again in FIG. 7 with the exception of part 65. FIG. 7 shows the dimensions in millimeters(mm) of particular aspects of the flow restrictor 60. O-ring 66 fits over a guide channel ( not shown ) with a diameter of 42 millimeters. A standard KF-40 O-ring can be used in this instance. The overall dimensions and shape of the flow restrictor 60 are not critical and can vary for other embodiments according to the particular connection needs, for example, conduit connection needs of conduit ends 112,122 and 52 and the particular needs of clamp 130, all of which are illustrated in FIG. 3. The inside circular diameters in millimeters of flow path 62 and flow path 64 are shown in FIG. 7. In this particular embodiment, the inside diameter of flow path 62 is 7 millimeters and that of flow path 64 is 9 millimeters. This provides an opening area ratio of 1.65 when the opening area of flow path 64 is divided by the opening area of flow path 62. This is a particularly preferred opening area ratio for this embodiment of the flow restrictor 60. The opening area ratio is preferably from 1.0 to 2.0, more preferably from 1.5 to 1.80 and most preferably from 1.6 to 1.7 for this embodiment of the flow restrictor 60. It should also be recognized that other opening area ratios are also useful for other embodiments of the flow restrictor 60. Also, it should be recognized that it is the proper ratio of overall flow rates through the two flow paths 62 and 64 which is most important. The proper ratio of flow rates is affected by additional factors and thus can be achieved in several ways in addition to adjusting the opening areas of flow paths 62 and 64. For example, the length and inside diameter of a lumen device will affect flow through flow path 62 and thus is also important for achieving a proper ratio of flow rates. The length of conduit 50 and opening size of conduit end 52 will also affect flow rate through flow path 62 and thus should also be taken under consideration. As examples of the foregoing, insufficient pressure differential and hence insufficient flow of the vapor sterilant out of the lumen and through flow path 62 will occur if the opening area or flow rate of flow path 64 is too large in relation to the opening area or flow rate of flow path 62. This will result in incomplete sterilization. Insufficient flow of the sterilant vapor out of the lumen and through flow path 62 will also occur if the opening area or flow rate of flow path 62 is too small in an absolute sense. This will also result in incomplete sterilization. Thus, a minimum opening area or flow rate is required for flow path 62. This can be determined by ordinary testing methods. Conversely, the lumen of a medical device may collapse with the vacuum pump on, if the opening area or flow rate of flow path 62 is too large in relation to the opening area or flow rate of flow path 64. Lumen collapse is to be avoided as this may irreversibly damage the lumen and device. Generally, the ratio of the opening areas or flow rates of the two flow paths is adjusted such that the sterilization vapor exhaust flow through both flow paths results in maximum efficiency of sterilization of the device to be sterilized while at the same time preserving the integrity of the device without unduly lengthening the exhaust flow time. Maximum efficiency of sterilization is defined herein as the ordinary english language usage of at the phrase. Maximum efficiency of sterilization is, for example, achieving sterilization with the minimum sterilant exposure and energy input. The opening areas for flow path 62 and flow path 64 need not be circular, as long as the basic flow requirements are met along with all connection requirements. Additionally, more than one opening for both flow path 62 and flow path 64 may be employed, as long as the sum of the combined flow paths is such that the flow rate requirements are met along with all connection requirements. Additionally, the vapor exhaust flow restrictor and the apparatus of the present invention may be constructed so that flow path 64 may be connected to multiple continuously open flow paths leading into and out of the sterilization chamber in various locations so that air vented into the sterilization chamber through path 64 is vented into the chamber in more than one location to maximise mixing. Similarly, with such a construction, the exhaust flow from the chamber through path 64 would be exhausted from more than one location. The foregoing construction may be achieved with a simple "T" shaped conduit with one end of the "T" leading into the sterilization chamber side of flow path 64 and the other ends of the "T" connecting to two conduits leading to two locations inside the sterilization chamber.

FIGS. 8a and 8b are side views of another preferred embodiment of the vapor exhaust flow restrictor 60 of FIG. 3. FIGS. 8a and 8b show the same parts and the relationship between these parts under different conditions. FIG. 8a illustrates the flow restrictor 60 of this embodiment in its condition under low exhaust flow through flow path 64, whereas FIG. 8b illustrates the flow restrictor 60 of this embodiment in its condition under high exhaust flow through flow path 64. In this embodiment, the vapor exhaust flow restrictor 60 of FIG. 3 comprises all parts illustrated in FIG. 3 and further comprises the conduit with end 65 leading to flow path 62. End 65 is designed as in other embodiments of the vapor exhaust flow restrictor 60 with the appropriate outside diameter to fit tightly inside the vapor exhaust flow restrictor end 52 of the gas and vapor flow conduit 50 of FIG. 3 without pressure loss. The embodiment of the vapor exhaust flow restrictor 60 of FIGS. 8a and 8b further comprises a movable slider valve 71 which is connected to hinge 72. Hinge 72 is connected via connector arm 73 to pivot 74. The slider valve 71 is placed in a location inside conduit 61 which is connected to flow path 64. The slider valve 71 is placed so that it is movable and can act as a valve to control the exhaust flow of gas flowing through flow path 64. Also shown in both FIGS. 8a and 8b is a vane 76 which is connected to a connector arm 75, which in turn is connected to pivot 74. Vane 76 is illustrated in side view in FIGS. 8a and 8b. However, vane 76 comprises a surface which will respond to the pressure of the air and sterilant vapor exhaust flow which flows through flow path 64. Vane 76 is placed so that it can respond to the amount of gas flow occurring through flow path 64. Also shown connected to pivot 74 is pendulum arm 77 and pendulum ball 78. Pivot 74 and the entire construction is supported by bracket 79 which is connected to the appropriate location on the flow restrictor 60. Under conditions of low exhaust flow occurring through flow path 64, there will be no appreciable gas pressure on the surface of vane 76. Therefore, slider valve 71 will be in its most open position, thus allowing the maximum amount of the air and sterilant vapor mixture to flow out of the sterilization chamber through flow path 64. This is illustrated in FIG. 8a. FIG. 8b illustrates the location of slider valve 71 and vane 76 under high exhaust flow conditions through flow path 64. In this situation, there is a sufficient pressure on the surface area of vane 76 such that the entire construction pivots around pivot 74 moving slider valve 71 to its most closed position inside conduit 61. Even under its most closed condition inside conduit 61, slider valve 71 will still allow a small amount of air and sterilant vapor mixture to flow through flow path 64. This can occur either through the appropriate placement of slider valve 71 under its most closed condition or alternatively it can be achieved via the construction of openings in the surface of slider valve 71. The pendulum arm 77 and pendulum ball 78 will return the slider valve 71 and vane 76 construction to the original most open position for slider valve 71 under conditions where there is insufficient gas pressure on vane 76 to move slider valve 71 to its most closed position illustrated in FIG. 8b. Thus, the purpose of the entire apparatus illustrated in FIGS. 8a and 8b is to more carefully control the exhaust flow occurring through flow path 64. High exhaust flow occurring through flow path 64 will be dampened or diminished by the slider valve and vane apparatus. Conversely, low flow occurring through flow path 64 will be unimpeded. In this way, a further automatic control of exhaust flow through flow path 64 can be implemented. The entire purpose of this additional construction illustrated in FIGS. 8a and 8b is to further optimize the entire sterilization process. High exhaust flow occurring through flow path 64 will be dampened, thus optimizing exhaust flow through flow path 62 which is connected to the lumen of the device to be sterilized. Thus, sterilization efficiency will be enhanced without significantly compromising rate of sterilization chamber exhaust. Similarly, under low flow conditions occurring through flow path 64, sterilization efficiency will not be adversely effected, since adequate flow will still occur through flow path 62 which is connected to the lumen of the device to be sterilized. The entire apparatus illustrated in FIGS. 8a and 8b can be constructed with conventional metal and plastic parts with known techniques of construction. Other types of valves may also be utilized for regulating the flow through flow path 64. These other types of valves include conventional valves known in the art of gas flow regulation.

FIG. 9 is a perspective view of a preferred embodiment of the gas and vapor flow conduit 50 of the sterilization apparatus 10 of the invention. The gas and vapor flow conduit 50 is shown along with the lumen connector end 51. Lumen connector end 51 is constructed for releasible connection to a lumen via conventional techniques. Alternatively, lumen connector end 51 can be constructed for releasible connection to open ends of diffusion restricted areas or lumens of multiple devices simultaneously, again via conventional techniques. A rack 140 for holding lumen devices and other articles to be sterilized is also shown. Rack 140 is located inside the sterilization chamber 20 illustrated in FIGS. 1 and 2.

FIG. 10 is a graph of one embodiment of the method of the sterilization cycle of the present invention which corresponds to the embodiment of the apparatus of the invention illustrated in FIGS. 1, 3–7 and 9. In this embodiment, the article to be sterilized, such as a medical device with a long narrow lumen with at least two open ends, is placed within a sterilization chamber 20. One open end of the lumen is connected via a gas and vapor conduit 50 to the vapor exhaust flow restrictor 60 which is fixed in place between the exhaust port 24 of the sterilization chamber 20 and the vacuum pump valve 80. The pressure in the sterilization chamber 20 is reduced to 400 millitorr over a five minute period. A volume of a solution of hydrogen peroxide which equates to a chamber concentration of 6 mg/liter hydrogen peroxide when vaporized is injected into the chamber 20 with a conventional liquid injector 40. The hydrogen peroxide solution vaporizes and the vapor is allowed to fully diffuse into the chamber for a diffusion contact time of 50 minutes. The pressure eventually achieved at this stage of course depends upon the load of articles to be sterilized in the chamber. The vacuum pump 70 is turned on and the pressure in the chamber is lowered to 500 millitorr. The sterilant vapor is pulled through the lumen and the sterilization chamber exhaust port 24 during this step. A plasma is then created with conventional radio frequency energy input for 15 minutes. Air is then vented directly into the sterilization chamber 20 until atmospheric pressure is achieved.

FIG. 11 is a graph of another embodiment of the method of the sterilization cycle of the present invention which corresponds to the embodiment of the apparatus of the invention illustrated in FIGS. 1, 3–7 and 9. In this embodiment, the article to be sterilized, such as a medical device with a long narrow lumen with at least two open ends, is placed within a sterilization chamber 20 with an internal volume of 173 liters. One open end of the lumen is connected via a gas and vapor conduit 50 to the vapor exhaust flow restrictor 60 which is fixed in place between the exhaust port 24 of the sterilization chamber 20 and the vacuum pump valve 80. A vacuum with a pressure of 400 millitorr is then created. This stage also serves to remove moisture from the system. At this time, a volume of a solution of hydrogen peroxide which equates to a chamber concentration of 6 mg/liter hydrogen peroxide when vaporized is injected into the chamber 20 with a conventional liquid injector 40. The hydrogen peroxide solution vaporizes and the hydrogen peroxide remains in the vapor state and is allowed to fully diffuse into the chamber over an eight minute period. Air is then vented into the sterilization chamber 20 through valve 90 into conduit 120 leading to the vacuum pump valve 80 from the air inlet and vapor exhaust flow restrictor 60 and through a continuously open flow path 64 in the vapor exhaust flow restrictor 60. Air is vented into the chamber 20 until atmospheric pressure is achieved. The air and sterilant vapor mixture is allowed to fully diffuse through the lumen for an additional diffusion contact time of two minutes. The vacuum pump 70 is turned on once again and the pressure in chamber 20 is reduced to 500 millitorr. A high sterilization vapor exhaust flow is created during this time through the lumen as well as the sterilization chamber exhaust port 24 by the vapor exhaust flow restrictor 60 with flow restrictor flow paths 62 and 64. A plasma is then created with conventional radio frequency energy input for 2 minutes. A final air vent to atmospheric pressure completes the cycle.

The following tests were performed to illustrate the importance of the exhaust flow path 64 of the flow restrictor of the invention on the achievement of rapid sterilization chamber exhaust. These tests are described below in example 1.

EXAMPLE 1

Tests were completed to compare the sterilization chamber exhaust efficacy of the sterilization apparatus and method of the present invention embodied in FIGS. 1, 3–7, 9 and 11 with the exception that conduit 50 was omitted, compared to an apparatus and method which did not employ the invention.

Three tests were conducted: tests A, B and C. In tests A and B, one end of a 100 cm length of polyethylene simulated-lumen with an internal diameter of approximately 5 mm was connected directly to flow path 62 of the vapor exhaust flow restrictor 60 without utilizing conduit 50 and processed utilizing the apparatus and method of the invention embodied in FIGS. 1, 3–7, 9 and 11 with the following changes: test A: no changes, exhaust flow was conducted through both flow paths 62 and 64; and test B: flow path 64 was plugged, so that all exhaust flow was directed through the simulated lumen and flow path 62. In test C, no lumen was employed and both conduit 50 and flow restrictor 60 were omitted. Thus, test C was a control test of the most rapid sterilization chamber exhaust possible without any exhaust flow restriction whatsoever. A sterilizer apparatus containing a vacuum chamber with a volume of 173 liters was utilized for these tests. The results were as follows:

TABLE 1

Effect of Flow Restrictor Flow Path 64 on Sterilization Chamber Exhaust Time

| Test | 1st Vacuum Pump Down (to 500 mtorr) | 2nd Vacuum Pump Down (to 500 mtorr) |
| --- | --- | --- |
| A (64 open) | 4 min, 42 sec | 4 min, 42 sec |
| B (64 plugged) | 9 min, 9 sec | 9 min, 3 sec |
| C (control) | 4 min, 40 sec | 4 min, 46 sec |

The above results show that when flow path 64 is plugged, the time to exhaust the chamber is approximately twice the time required to exhaust the chamber when flow path 64 is open. Additionally, the results show that when flow path 64 is open, the time to exhaust the chamber is not reduced from the time required to exhaust the chamber without the flow restrictor of the invention. Since the usage of the flow restrictor and other aspects of the invention produce sterilant vapor contact and partial removal through a lumen or other device, improved sterilization performance can be achieved without lengthening the time required for sterilization.

The following tests were performed to illustrate the importance of the flow restrictor flow path opening area ratio for one embodiment of the apparatus and method of the invention. These tests are described below in Example 2.

EXAMPLE 2

A series of test flow restrictors were constructed from aluminum so that the flow restrictor flow path 64 and flow path 62 opening areas could be easily varied by drilling holes of various sizes for each flow path and the effect of the 64/62 opening area ratio on the amount of vacuum pull at the lumen side of the exhaust flow path 62 could be determined. Various flow restrictors with different opening area ratios were constructed and placed between two conduits, one leading to a vacuum pump and the other leading to a lumen device constructed from flexible thin wall polyethylene tubing. The vacuum pump was turned on and the effect of the lumen as well as the ability to produce an acceptable vacuum pull without the lumen in place determined. An acceptable vacuum pull occurred when a small paper valve material placed over the lumen side of flow path 62 was held tightly in place by the applied negative pressure. The results were as follows:

Effect of Flow Restrictor Flow Paths 64/62 Opening Area Ratio
on Vacuum Pull at Lumen Side of Exhaust Flow Path 62

| Opening Area Ratio Flow Paths 64/62 | Vacuum Pull/Observations |
|---|---|
| 0.1 | inward flexing of lumen |
| 0.90 | inward flexing of lumen |
| 1.00 | + (acceptable pull) |
| 1.50 | + |
| 1.60 | + |
| 1.70 | + |
| 1.80 | + |
| 2.00 | + |
| 2.10 | +/− (unnacceptable pull) |
| 2.50 | − no pull |
| 3.00 | − |

It can be seen from the above results that the opening area ratio of flow path 64 divided by flow path 62 is between 1.0 and 2.0 for acceptable operation of one embodiment of the flow restrictor.

Tests were completed to compare the sterilization efficacy of the sterilization apparatus and method of the present invention embodied in FIGS. 1, 3–7, 9 and 10 compared to an apparatus and method not employing the invention. These tests are described below in examples 3 and 4.

EXAMPLE 3

A biological challenge consisting of 1.7×10e6 B. stearothermophilus spores inoculated on stainless steel scalpel blades was used for comparative sterilization efficacy tests. An inoculated blade was placed inside a teflon center piece of 1.3 cm ID and 5 cm length. This center piece was connected on both sides via rubber septa to a 100 cm length of polyethylene simulated-lumen with an internal diameter of 1 mm. The entire lumen was 205 cm in length, including a 5 cm center piece. Two samples were prepared: test sample A and control sample B. One end of the lumen of test sample A was connected via the gas and vapor conduit to the vapor exhaust flow restrictor and processed utilizing the apparatus and method of the invention for sterilization embodied in FIGS. 1, 3–7, 9 and 10. A sterilizer apparatus containing a vacuum chamber with a volume of 173 liters was utilized for these tests. The lumen of control sample B was not connected via a gas and vapor conduit to the vapor exhaust flow restrictor of the invention, but was otherwise processed identically to test sample A in the same apparatus. Following the final air venting to atmospheric pressure, the blades were removed from the teflon center pieces and tested for sterility. The results were as follows:

TABLE 3

Effect of the Apparatus and Method of the Present Invention
on Sterilization of Simulated Narrow Lumens

| | Recovery of Viable Organisms (Day) | | | | | | |
|---|---|---|---|---|---|---|---|
| Sample | 1 | 2 | 3 | 4 | 5 | 6 | 7 | 14 |
| A (test) | − | − | | − | − | | | − |
| B (control) | − | + | | + | + | | | + |

The results show that the apparatus and method of the present invention achieve complete sterilization of a simulated long narrow lumen device and that sterilization cannot be achieved without employing the complete apparatus and method of the invention. The results clearly show the importance of the proper flow path connection requirements of the invention.

EXAMPLE 4

The sterilization apparatus and methods of Example 3 were utilized to test the sterilization efficacy of the apparatus and method of the present invention with simulated endoscope devices. These simulated devices were constructed of plastic tubing and contained the following essential endoscope elements, all of which were tested for sterility in one location: universal airway (UA), universal suction (US), universal water (UW), insertion airway (IA), insertion suction (IS) and insertion water (IW). Sterility was assessed in one location within each simulated endoscope element by placing a biological indicator consisting of 1.7×10e6 B. stearothermophilus spores inoculated on a stainless steel scalpel blade inside a container and placing this container in the particular location to be assessed. These locations are known in the art and are known to be particularly difficult to sterilize. Two simulated endoscopes were tested for sterilization utilizing the endoscope sterility test methods of Example 3. One test sample was connected via a gas and vapor conduit to a flow restrictor according to the apparatus and method of the present invention. A control sample was not connected via a gas and vapor conduit to the vapor exhaust flow restrictor of the invention, but was otherwise processed identically to the test sample in the same apparatus. The test was repeated once for test samples only. The sterility test results were as follows:

TABLE 4

Effect of the Apparatus and Method of the Present Invention
on Sterilization of Simulated Endoscopes

| Sample | Recovery of Viable Organisms (Day) | | Sample | Recovery of Viable Organisms (Day) |
|---|---|---|---|---|
| | 1 | 14 | | 1 |
| Test UA | − | − | Control UA | + |
| Test US | − | − | Control US | + |
| Test UW | − | − | Control UW | + |
| Test IA | − | − | Control IA | + |
| Test IS | − | − | Control IS | + |
| Test IW | − | − | Control IW | + |

The results show that the apparatus and method of the present invention achieve complete sterilization of a simulated endoscope device and that sterilization cannot be achieved without employing the complete apparatus and method of the invention.

Tests were completed to compare the sterilization efficacy of the sterilization apparatus and method of the present invention embodied in FIGS. 1, 3–7, 9 and 11 compared to an apparatus and method which did not employ the invention. These tests are described below in examples 5 and 6.

EXAMPLE 5

A biological challenge consisting of 1.7×10e6 B. stearothermophilus spores inoculated on stainless steel scalpel blades was used for comparative sterilization efficacy tests. An inoculated blade was placed inside a teflon center piece of 1.3 cm ID and 5 cm length. This center piece was connected on both sides via rubber septa to a 100 cm length of polyethylene simulated-lumen with an internal diameter of 1 mm. Thus, the entire lumen was 205 cm in length including a 5 cm center piece. Two samples were prepared: test sample A and control sample B. One end of the lumen of test sample A was connected via the gas and vapor conduit to the vapor exhaust flow restrictor and processed utilizing the apparatus and method of the invention for sterilization embodied in FIGS. 1, 3–7, 9 and 11. A sterilizer apparatus containing a vacuum chamber with a volume of 173 liters was utilized for these tests. The lumen of control sample B was not connected via a gas and vapor conduit to the vapor exhaust flow restrictor of the invention, but was otherwise processed identically to test sample A in the same apparatus. Following the final air venting to atmospheric pressure, the blades were removed from the teflon center pieces and tested for sterility utilizing standard culture and microbiology test methods. Samples were cultured and tested for recovery of viable colony forming units (organisms) over a 14 day period. A (+) indicates positive recovery of viable organisms and hence lack of complete sterilization. A (-) indicates no recovery and thus complete sterilization. The results were as follows:

TABLE 5

Effect of the Apparatus and Method of the Present Invention on Sterilization of Simulated Narrow Lumens

| Sample | Recovery of Viable Organisms (Day) | | | | | | | |
|---|---|---|---|---|---|---|---|---|
| | 1 | 2 | 3 | 4 | 5 | 6 | 7 | 14 |
| A (test) | - | - | | - | - | | | - |
| B (control) | - | + | | + | + | | | + |

The results show that the apparatus and method of the present invention achieve complete sterilization of a simulated long narrow lumen device and that sterilization cannot be achieved without employing the complete apparatus and method of the invention. The results clearly show the importance of the proper flow path connection requirements of the invention.

EXAMPLE 6

The sterility test methods and sterilization apparatus and methods of Example 5 were utilized to test the sterilization efficacy of the apparatus and method of the present invention with simulated endoscope devices. These simulated devices were constructed of plastic tubing and contained the following essential endoscope elements, all of which were tested for sterility in one location: universal airway (UA), universal suction (US), universal water (UW), insertion airway (IA), insertion suction (IS) and insertion water (IW). Sterility was assessed in one location within each simulated endoscope element by placing a biological indicator consisting of 1.7×10e6 B. stearothermophilus spores inoculated on a stainless steel scalpel blade inside a container and placing this container in the particular location to be assessed. These locations are known in the art and are known to be particularly difficult to sterilize. Two simulated endoscopes were tested for sterilization. One test sample was connected via a gas and vapor conduit to a flow restrictor according to the apparatus and method of the present invention. A control sample was not connected via a gas and vapor conduit to the vapor exhaust flow restrictor of the invention, but was otherwise processed identically to the test sample in the same apparatus. The test was repeated once for test samples only. The sterility test results were as follows:

TABLE 6

Effect of the Apparatus and Method of the Present Invention on Sterilization of Simulated Endoscopes

| Sample | Recovery of Viable Organisms (Day) | | Sample | Recovery of Viable Organisms (Day) |
|---|---|---|---|---|
| | 1 | 14 | | 1 |
| Test UA | - | - | Control UA | + |
| Test US | - | - | Control US | + |
| Test UW | - | - | Control UW | + |
| Test IA | - | - | Control IA | + |
| Test IS | - | - | Control IS | + |
| Test IW | - | - | Control IW | + |

The results show that the apparatus and method of the present invention achieve complete sterilization of a simulated endoscope device and that sterilization cannot be achieved without employing the complete apparatus and method of the invention.

The foregoing examples are provided by way of illustration only and are not intended as a limitation of the present invention, many variations of which are possible without departing from the spirit and scope thereof. The present invention provides several advantages over earlier vapor sterilization systems, such as: (1) the rapid and safe sterilization of a variety of lumened devices with both large and narrow lumens can be achieved at low temperatures without a complex apparatus or multiple pulses of sterilant vapor; and (2) the need to attach a special vessel to deliver sterilant vapors into long, narrow lumens is eliminated. The apparatus and method of the present invention therefore provides for a highly efficient and relatively inexpensive apparatus and method of sterilization.

What is claimed is:

1. An apparatus for sterilizing the interior and exterior of a device with at least two open ends and a flow path therebetween, comprising:
    (a) a sterilization chamber having an exhaust port;
    (b) a source of liquid or vapor sterilant, adapted to provide said sterilant in said sterilization chamber;
    (c) a vacuum source with a vacuum valve to create a sterilization vapor from said sterilant, a negative pressure differential at said exhaust port of said sterilization chamber and an exhaust flow path out of said chamber;
    (d) a vapor exhaust flow restrictor having at least a first and a second flow path; and
    (e) a gas and vapor flow conduit connecting one of said open ends of said device to the first flow path of the vapor exhaust flow restrictor,
    wherein said vapor exhaust flow restrictor allows part of the sterilization vapor to flow through said flow path of said device, through said gas and vapor flow conduit, through said first flow path of said vapor exhaust flow restrictor, and thereafter out of said sterilization chamber through said vacuum valve and vacuum source and wherein the remainder of the sterilization vapor flows directly out of said sterilization chamber through the second flow path of said exhaust flow restrictor and through said vacuum valve and vacuum source without passing through said flow path of said device and said gas and vapor flow conduit.

2. The apparatus of claim 1, wherein said device is a lumen.

3. The apparatus of claim 1, wherein said sterilant is from the group consisting of hydrogen peroxide and peracetic acid.

4. The apparatus of claim 1, wherein said source of sterilant is selected from the group consisting of an injector, a liquid flow-through device, a liquid reservoir and aerosol spray device.

5. The apparatus of claim 1, wherein said source of sterilant is placed inside said chamber.

6. The apparatus of claim 5, wherein said source of sterilant is a liquid reservoir placed inside the chamber.

7. The apparatus of claim 1, wherein said gas and vapor flow conduit is constructed for releasible connection.

8. The apparatus of claim 7, wherein said gas and vapor flow conduit connects one of said two open ends of multiple devices simultaneously to said first flow path of said vapor exhaust flow restrictor, said first flow path allowing exhaust flow out of said sterilization chamber through said vacuum valve and vacuum source.

9. The apparatus of claim 1, wherein said first and second flow paths each have an opening with an opening area, and wherein said first flow path is a continuously open flow path open to flow in both directions and which allows exhaust flow out of said sterilization chamber through said vacuum valve and vacuum source.

10. The apparatus of claim 9, wherein said first flow path is constructed with multiple conduits connected to said sterilization chamber side of said flow path, wherein said conduits allow air venting and exhaust flow into and out of said chamber respectively, from more than one location inside said chamber.

11. The apparatus of claim 9, wherein said first flow path further comprises a valve, said valve being capable of opening or closing said first flow path.

12. The apparatus of claim 9, wherein said second flow path allows flow only in the direction of said sterilization chamber exhaust port allowing exhaust flow out of said sterilization chamber through said vacuum valve and vacuum source and which does not allow the influx of air from outside said sterilization chamber and wherein said second flow path is connected to said gas and vapor flow conduit and through said conduit to one of said two open ends of said device to be sterilized.

13. The apparatus of claim 12, wherein the ratio of said flow of said first flow path to said flow of said second flow path is such that the sterilization vapor exhaust flow through said first and second flow paths results in maximum efficiency of sterilization of said device to be sterilized.

14. The apparatus of claim 12, wherein the ratio of said opening area of said first flow path to said opening area of said second flow path is between 1.0 and 2.0.

15. The apparatus of claim 12, wherein the ratio of said opening area of said first flow path to said opening area of said second flow path is 1.65.

16. The apparatus of claim 12, wherein said vapor exhaust flow restrictor has more than one opening for each flow path.

17. The apparatus of claim 1, wherein said vacuum source is a vacuum pump.

18. The apparatus of claim 1, wherein the sterility of said device is maintained following sterilization with an enclosure, wherein said enclosure completely encloses said device.

19. The apparatus of claim 18, wherein the enclosure comprises a flexible material.

20. The apparatus of claim 19, wherein said flexible material is comprised of non-woven polypropylene.

21. A method for sterilizing the interior and exterior of a device with at least two open ends and a flow path therebetween, comprising the steps of:
(a) placing said device into a sterilization chamber having an exhaust port;
(b) connecting one of said open ends of said device to a first end of a gas and vapor flow conduit having a first and second end, the second end of which is connected to a first flow path of a vapor exhaust flow restrictor having at least two flow paths, said first flow path of said vapor exhaust flow restrictor allowing exhaust flow out of said sterilization chamber through a vacuum valve and vacuum source;
(c) introducing a liquid or vapor sterilant into said sterilization chamber;
(d) exposing said device to negative pressure with the use of said vacuum source for a time sufficient to provide sterilization vapor directly to the interior and exterior of said device, wherein said exposing can be before or after said introducing in step (c);
(e) exposing said device to negative pressure with the use of said vacuum source to create a negative pressure differential at said exhaust port of said sterilization chamber and the use of said vapor exhaust flow restrictor for a time sufficient so that part of said sterilization vapor flows through said flow path of said device to sterilize said devices, through said gas and vapor flow conduit, and out of said sterilization chamber and the remainder of said sterilization vapor flows directly out of said sterilization chamber without passing through said gas and vapor flow conduit and said flow path of said device.

22. The method of claim 21, wherein said device is a lumen.

23. The method of claim 21, wherein said sterilant is from the group consisting of hydrogen peroxide and peracetic acid.

24. The method of claim 21, wherein said introducing of said sterilant comprises delivery via one or more methods selected from the group consisting of injection, liquid flow-through, a liquid reservoir and aerosol spray.

25. The method of claim 21, further comprising the step of exposing said device to a plasma after step (d) or prior to or after step (e).

26. The method of claim 25, wherein said plasma is generated in a second, separate chamber and said method further comprises the step of flowing said plasma into said sterilization chamber.

27. The method of claim 21, further comprising warming said device to be sterilized in said sterilization chamber prior to step (c).

28. The method of claim 27, wherein said device to be warmed is warmed with an applied electric field at low pressure.

29. The method of claim 27, further comprising the step of exposing said device to a plasma following step (e).

30. The method of claim 29, wherein said plasma is generated in a second, separate chamber and said method further comprises the step of flowing said plasma into said sterilization chamber.

31. The method of claim 21, further comprising the step of enclosing said device completely in an enclosure prior to step (a) to maintain the sterility of said device following sterilization.

32. The method of claim 31, wherein said enclosure is comprised of non-woven polypropylene.

33. The method of claim 21, wherein steps (c) through (e) are repeated one or more times.

34. The method of claim 21, further comprising the step between the first and second exposing steps (d) and (e) of venting air directly into said sterilization chamber for a time sufficient for the air and sterilization vapor mixture to come in close contact with said device to be sterilized.

35. The method of claim 34, wherein steps (c) through (f) are repeated one or more times.

36. The method of claim 21, further comprising the step between the first and second exposing steps (d) and (e) of venting air through said second flow path in said vapor exhaust flow restrictor of step (b), said second flow path continuously open to said sterilization chamber, for a time sufficient for the air and sterilization vapor mixtures to come in close contact with said device to be sterilized.

37. The method of claim 36, wherein steps (c) through (f) are repeated one or more times.

* * * * *

UNITED STATES PATENT AND TRADEMARK OFFICE
CERTIFICATE OF CORRECTION

PATENT NO. : 5,869,000
DATED : February 9, 1999
INVENTOR(S) : Kevin Richard Decato It is certified that error appears in the above-indentified patent and that said Letters Patent is hereby corrected as shown below:

in Claim 21, Column 22, line, 28 change "devices" to --device--

In Claim 36, Column 24, line 3 change "path continuously" to --path being continuously--

Signed and Sealed this

Sixth Day of March, 2001

Attest:

NICHOLAS P. GODICI

*Attesting Officer*   *Acting Director of the United States Patent and Trademark Office*